United States Patent [19]

Rule et al.

[11] Patent Number: 4,895,992
[45] Date of Patent: * Jan. 23, 1990

[54] PROCESS FOR PREPARING IODINATED AROMATIC COMPOUNDS AND THE REGENERATION OF CATALYSTS USED THEREIN

[75] Inventors: Mark Rule; Gerald C. Tustin, both of Kingsport; Donald L. Carver, Church Hill; Jerry S. Fauver, Blountville, all of Tenn.

[73] Assignee: Eastman Kodak Company, Rochester, N.Y.

[ * ] Notice: The portion of the term of this patent subsequent to Dec. 20, 2005 has been disclaimed.

[21] Appl. No.: 246,154

[22] Filed: Sep. 19, 1988

Related U.S. Application Data

[63] Continuation of Ser. No. 70,249, Jul. 6, 1987, abandoned, which is a continuation-in-part of Ser. No. 29,898, Mar. 25, 1987, Pat. No. 4,792,642.

[51] Int. Cl.$^4$ .................. C07C 17/15; C07C 21/24; B01J 29/38; B01J 21/20

[52] U.S. Cl. .................................. 570/203; 502/38; 546/348; 549/49; 549/81; 549/505; 570/204; 570/206

[58] Field of Search .............. 570/203, 204, 206, 182, 570/183; 502/38, 41, 49, 52, 65, 66, 73, 79

[56] References Cited

U.S. PATENT DOCUMENTS

| | | | |
|---|---|---|---|
| 4,788,353 | 11/1988 | Paparatto et al. | 570/203 |
| 4,788,354 | 11/1988 | Paparatto et al. | 570/203 |
| 4,792,642 | 12/1988 | Rule et al. | 570/203 |

FOREIGN PATENT DOCUMENTS

| | | | |
|---|---|---|---|
| 0181790 | 5/1986 | European Pat. Off. | 570/206 |
| 0183579 | 6/1986 | European Pat. Off. | 570/203 |

*Primary Examiner*—Paul E. Konopka
*Attorney, Agent, or Firm*—Charles R. Martin; William P. Heath, Jr.

[57] ABSTRACT

A process for iodinating aromatic compounds by reacting an aromatic compound with oxygen at low temperatures in the presence of a non-acid catalyst containing an oxidation catalyst. The catalyst may be regenerated by heating the catalyst in the presence of oxygen.

16 Claims, No Drawings

PROCESS FOR PREPARING IODINATED AROMATIC COMPOUNDS AND THE REGENERATION OF CATALYSTS USED THEREIN

RELATED APPLICATIONS

This is a continuation of application Ser. No. 070,249, filed July 6, 1987, now abandoned, which application is a continuation-in-part of application Ser. No. 029,898, filed Mar. 25, 1987 now U.S. Pat. No. 4,792,642.

BACKGROUND OF THE INVENTION

1. Field of the Invention

The present invention relates to processes for iodinating aromatic compounds over non-acid catalysts wherein the activity of the catalysts at low temperatures is enhanced by the presence of an oxidation catalyst.

2. Discussion of Background

It has long been desired to be able to derivatize aromatic compounds and in particular condensed ring aromatic compounds in commercially attractive quantities since many of these compounds possess properties which would fill long sought needs. In particular, the compound 2,6-naphthalene dicarboxylic acid or its esters is particularly desired for use in the manufacture of polyesters which would have excellent barrier properties when fabricated into films, bottles or coatings. However, known techniques for producing 2,6-naphthalene dicarboxylic acid and esters are very expensive and impractical for commercial exploitation.

Synthesis of iodobenzene starting from benzene and iodine is usually carried out in the liquid phase in the presence of an oxidative agent, preferably nitric acid. Such techniques have been described in the literature and in particular in Japanese No. 58/77830, U.S.S.R. Pat. No. 453392 and by Datta and Chatterjee in the *Journal of the American Chemical Society*, 39, 437 (1917). Other oxidative agents have also been suggested but none of these have proven to be more efficient or convenient than nitric acid. Typical of the other oxidative agents which have been suggested are iodic acid, sulfur trioxide and hydrogen peroxide as described by Butler in the *Journal of Chemical Education*, 48, 508 (1971). The use of metal halogenides to catalyze iodination has been suggested by Uemura, Noe, and Okano in the *Bulletin of Chemical Society of Japan*, 47, 147 (1974). The concept of direct iodination of benzene in the gas phase over the zeolite 13X has been suggested in Japanese Patent Publication No. 82/77631 in the absence of any oxidizing agent.

Ishida and Chono in Japanese Kokai No. 59/219241 have suggested a technique for oxyiodinating benzene over very acidic zeolite catalysts having a silica to alumina ($SiO_2:Al_2O_3$) ratio of greater than 10. In this technique benzene is reacted with iodine in the presence of oxygen to produce iodinated benzene. According to this disclosure approximately 96% of the benzene which is converted to the iodinated form. However, the remaining benzene is oxidized to carbon dioxide and other combustion products resulting in the loss of valuable starting material.

Paparatto and Saetti disclosed in European Patent Applications Nos. 181,790 and 183,579 techniques for oxyiodination of benzene over zeolite catalysts. European Patent Application No. 181,790 suggests the use of ZSM-5 and ZSM-11 type zeolites which have been exchanged prior to use with the least one bivalent or trivalent cation. According to this disclosure the utilization of these zeolites in the acid or alkaline form results in a rapid decrease in catalytic activity in relatively few hours.

European Patent Application No. 183,579 suggests the utilization of X type or Y type of zeolite in non-acid form. According to 183,579 the X or Y zeolites have to be used in the form exchanged with monovalent, bivalent or trivalent cations and in particular with alkaline or rare earth cations. The techniques of 181,790 and 183,579 prepare the monoiodobenzene in selectivities in excess of 90% and only distinctly minor amounts of the diiodobenzene compounds.

Accordingly, a need exists for a process which can iodinate benzene at high conversions with substantially no oxidation of the benzene ring.

Further need exists for a process which selectively produces para-diiodobenzene with substantially no oxidation of the benzene ring.

Another need exists for a process which iodinates naphthalene preferentially at the 2-position with minimum formation of oxidation products.

A further need exists for a process which selectively produces 2,6-diiodonaphthalene with minimal oxidation of the naphthalene starting material.

RELATED APPLICATIONS

Copending applications Ser. Nos. 912,806, filed Sept. 29, 1986; 029,959, filed Mar. 25, 1987; 029,897, filed Mar. 25, 1987; and 029,896, filed Mar. 25, 1987 disclose techniques for iodinating aromatic compounds over non-acid catalysts. The selectivities of these techniques to the desired products are improved by conducting the techniques at comparatively low temperatures on the order of from about 100° C.–250° C. However, the activity of the catalysts is substantially reduced at these low temperatures as compared with the activity obtained at higher temperatures.

Accordingly, a need exists for a technique which optimizes both selectivity and catalyst activity.

Additionally, it has been found that the activities of these catalysts is reduced over time and that the catalysts are slowly deactivated as carbonaceous deposits accumulate on the catalyst. The original catalytic activity can be restored by burning off the carbon deposits at high temperatures. However, these high temperatures are difficult to obtain and maintain for long periods of time.

Accordingly, a need exists for a technique by which the catalyst can be regenerated at lower temperatures and shorter time periods.

BRIEF DESCRIPTION OF THE INVENTION

Accordingly, one object of the present invention comprises a technique for increasing the catalytic activity of zeolite catalysts utilized in the iodination of benzene.

Another object of the present invention comprise the techinque for increasing the activity of catalysts containing non-acidic sites utilized in the iodination of benzene.

Yet another object comprises a process for the selective iodination of benzene to para-diiodobenzene over a zeolite catalyst at high catalytic activity.

Yet a further object of the present invention comprises the technique of the iodination of naphthalene in the 2-position over a zeolite catalyst at high catalytic activity.

A further object of the present invention comprises a process for the selective iodination of naphthalene to 2,6-diiodonaphthalene over a zeolite catalyst at high activity.

Yet a further object of the present invention comprises a technique for the iodination of naphthalene in the 2-position over a catalyst containing non-acidic sites at high catalytic activity.

A further object of the invention is to provide a process for the improved regeneration of an iodination catalyst which uses lower temperatures and shorter regeneration times.

These and other objects of the present invention which will become apparent from the following disclosure have been attained by a process which comprises reacting an aromatic compound over an non-acid catalyst with a source of iodine and a source of molecular oxygen wherein the catalyst additionally contains an oxidation catalyst, and by a process for the improved regeneration of an iodination catalyst comprising the steps of incorporating an oxidation catalyst in an iodination catalyst to produce a combined catalyst and heating the combined catalyst at a temperature between about 250°–600° C.

DESCRIPTION OF THE PREFERRED EMBODIMENTS

The aromatic compounds which can be utilized in practice of the present invention are essentially any aromatic compound including substituted and unsubstituted aromatics. Suitable aromatic compounds include hydrocarbon aromatics, nitrogen containing aromatics, oxygen containing aromatics and sulfur containing aromatics. Typical hydrocarbon aromatics include benzene and biphenyl, and condensed ring aromatics such as naphthalene and anthracene; sulfur containing aromatics include thiophene and benzothiophene, nitrogen containing aromatics include aromatics such as pyridine and benzopyridine, oxygen containing aromatics including compounds such as furan and benzofuran; while substituted aromatics include diaryl sulfones, diaryl ethers, diaryl carbonyls, diaryl sulfides and the like. Aromatic compounds substituted by alkyl groups are generally not preferred for utilization in the present technique. It has been found that alkyl substituted aromatics are iodinated not only on the ring but also on the side chains. Further, the product obtained will also contain oxidized side chains and the like. Thus, while alkyl substituted aromatics can be utilized in the present technique their use is not preferred.

The catalysts which may be employed in the present technique are described in copending applications Ser. Nos. 912,806, filed Sept. 29, 1986; 029,959, filed Mar. 25, 1987; 029,897, filed Mar. 25, 1987; 029,896, filed Mar. 25, 1987; 029,899, filed Mar. 25, 1987 and 029,949, filed Mar. 25, 1987. The disclosure of these applications incorporated herein by reference for more complete description of the catalyst and reaction conditions which are to be employed.

The catalysts utilized in the present technique are generally characterized by containing non-acid sites, and more preferably basic sites. Non-zeolite catalysts generally do not exhibit the selectivity of the zeolite catalyst when producing polyiodinated products. Thus, when it is desired to produce para-diiodobenzene or 2,6-diiodonaphthalene it is preferred to employ a zeolite catalyst because of their greater selectivity.

The type of zeolite which is utilized is not critical so long as greater than 10% of exchange cations are alkali, alkaline earth or rare earth metals and the pore size is greater than about 6 Å. In general, the reaction rate is a function of silicon to aluminum ratio in the zeolite, since aluminum is part of the active site. It is preferred to use zeolites with a silicon (as Si) to aluminum (as Al) ratio of 10:1 or less, more particularly 5:1 or less, still more preferred are those zeolites having a silicon to aluminum ratio of 3:1 or less with the most preferred type having a silicon to aluminum ratio of 1.5 or less. Particular types of zeolites which have proven to be particularly effective are the X and Y types. The Y type zeolite generally has a silicon to aluminum ratio of about 1.5 to 1 to 3:1. The X type zeolite is generally considered to have a silicon to aluminum ratio of 1:1 to 1.5:1.

Most of the commercially available zeolites contain mainly sodium counter ions. However, alkali, alkaline earth and rare earth metal counter ion containing zeolites have all proven to be useful for the iodination of benzene. The alkali or alkaline earth metals containing zeolites are preferred because there is substantially no oxidation or burning of the benzene when these are used as the counter ions. The zeolites which have been ion exchanged with the rare earth metals show a higher burn rate which is generally not desired.

The counter ion is easily introduced into the zeolite by simple ion exchange, which is well known to those skilled in the art. This is generally accomplished by contacting in an aqueous medium a salt of the desired counter ion and the zeolite. The period of time over which the contact is conducted and a number of times the ion exchange process is performed is dependent upon the degree of replacement which is desired. Thus, one beginning with the zeolite in the sodium form may ion exchange this material with another counter ion to partially or substantially completely replace the sodium ion with a different counter ion.

The particular counter ion which is employed has an effect upon the product composition. The X type zeolite exhibits more sensitivity to the counter ion than the Y type does. That is, the selectivity of the X type zeolite to the production of specific mono, di or tri iodinated aromatic compounds can be altered more successfully with the selection of the appropriate counter ions than can the Y type. While not being bound to any particular theory it is believed that the counter ion affects the selectivity by altering the shape of the pore thereby increasing or decreasing the selectivity of the catalyst for any particular isomer as compared with the standard sodium form. As the number of cations at the exchange site decreases the effect of counter ions on the shape of the pore decreases and thus selectivity decreases. Thus, when one desires to produce a particular isomer high alumina content zeolites are preferred.

When the aromatic compound is a condensed ring aromatic such as naphthalene, it is preferred that the zeolite has been ion exchanged with sodium, potassium, rubidium and/or cesium and more preferably with potassium, rubidium or cesium. It has been found that when the zeolite is ion exchanged with lithium, calcium, strontium, barium or rare earth metals the condensed ring aromatics are oxidized by the oxygen present in the gas stream to a high degree at temperatures of 250° C. or above. It was surprising to discover that with potassium, rubidium and cesium the degree of naphthalene oxidation is significantly less than 1% of the naphthalene converted. That is, essentially no oxidation of naphthalene occurs with these counter ions. When the zeolite is essentially in the sodium form, oxidation of the naphthalene occurs but to a lesser extent than with lithium, calcium, strontium, barium and rare earth metal counter ions. In view of the higher oxidation rate is preferred that the zeolite be ion exchange with potassium, rubidium, and/or cesium such that at least 50% of the sodium ions are replaced by one or more of potassium, rubidium or cesium.

When one desires to produce the 2,6-diiodonaphthalene compound the 13 X type zeolite is preferred. The most preferred zeolite to produce the 2,6-diiodonaphthalene is the 13 X type which has been ion exchanged with potassium, rubidium or cesium. The ratio of 2,6- to 2,7-diiodonaphthalene generally increases with increasing amounts of these ions. The preferred counter ions for the production of p-diiodobenzene are sodium, potassium, rubidium and cesium and barium. From a cost standpoint, potassium is the most preferred counter ion for the production of p-diiodobenzene although rubidium and cesium are equally effective.

Typical non-zeolite catalysts are alkali or alkaline earth cations on inert supports. Suitable supports include alumina, silica, silica-alumina, titania, etc. The alkali or alkaline earth cations can be deposited on the support by any suitable technique, such as impregnation or ion exchange from aqueous solution.

These catalysts may be supported or unsupported or bound together with a binder to form a shaped particle. Typical supports and binders include silica, alumina, various clays and the like. In general, any material not containing acid sites can be utilized as the support. It is also possible to utilize the catalyst in powder form, especially when the reaction is to be conducted in a fluidized bed or in the liquid phase wherein the catalyst would be suspended in the liquid reactant.

In general, the catalyst selectivity increases with decreasing reaction temperature, however, catalyst activity also decreases with decreasing temperature. In order to increase the catalytic activity at low temperatures, it is desirable to incorporate in the catalyst an oxidation catalyst to produce a combined catalyst in an amount sufficient to increase the reaction rate. As oxidation catalyst one may use essentially any metal having a variable valence. The metals may be added in the form of an oxide, salt, or acid form and achieve the desired results. Suitable oxidation catalysts include manganese, iron, copper, ruthenium, rhodium, chromium, vanadium, arsenic, antimony, cobalt, boron and molybdenum. The form in which these materials are added to the reactor is not critical and may be added in the form of oxides, salts, acids and the like. Examples of catalysts include manganese chloride, iron sulfate, potassium molybdate, boric acid, cobalt chloride and the like. The oxidation catalyst can be supported on the iodination catalyst by any suitable technique, such as ion exchange or impregnation.

The amount of oxidation catalyst to be incorporated with the iodination catalyst is chosen so as to effectively increase the activity of the iodination catalyst. Generally, the amount of oxidation catalyst necessary is less than 1% by weight of the iodination catalyst although greater quantities may be used if desired. The utilization of oxidation catalyst in excess of 1% does not offer any increased activity over the utilization of lesser amounts. The use of great excesses of oxidation catalyst should be avoided since these catalysts occupy some of the active sites on the iodination catalyst and if used in greater excesses can actually reduce the catalyst activity by eliminating active sites. The preferred quantity of oxidation catalyst which is employed is less than 1% by weight of the iodination catalyst and more preferably less than 0.5 wt. %. The minimum amount of oxidation catalyst employed is that necessary to increase the catalytic activity of the iodination catalyst at the reaction temperature of interest. In general, the higher the reaction temperature the lower the quantity of oxidation catalyst which is necessary.

Without being bound by any particular theory, it is believed that the oxidation catalyst facilitates the reactivation of the basic catalyst by the oxygen. During the iodination reaction, $\frac{1}{2}$ mole of iodine becomes associated with the active site on the iodination catalyst and $\frac{1}{2}$ mole is utilized to iodinate the aromatic compounds. The oxygen reactivates the catalyst by releasing the iodine which is then free to react with additional aromatic compounds.

The temperature which the reaction is to be conducted is not critical and can be any temperature at which the aromatic compound is fluid. The maximum temperature at which the process can be carried out is that at which combustion of the aromatic compound occurs. Generally, temperatures of from about 100° to 500° C. have been found satisfactory, with temperatures of from 200° to 400° C. being preferred, preferably from about 200° to 250° C. When operating at the lower ranges, the oxidation catalyst have their greatest effect in increasing the activity of the iodination catalyst. Surprisingly, the presence of the oxidation metals do not significantly increase the degree of combustion of the aromatic compounds. This is especially unexpected for naphthalene, since these same oxidation metals are utilized in processes for the partial combustion of naphthalene.

The pressure at which the process is conducted is not critical and can range from subatmospheric to superatmospheric. The utilization of elevated pressures in the gas phase process may be preferred so as to minimize equipment size. In general, pressures from atmospheric to 600 psig have proven satisfactory although higher or lower pressures can be utilized.

The molecular oxygen can be introduced as pure oxygen, air or oxygen diluted with any other inert material such as carbon dioxide or water vapor. Essentially oxygen from any convenient source may be utilized. The purpose of the oxygen is to regenerate the active site on the zeolite to its active form once the iodination reaction has occurred. Thus, the amount of oxygen present during the reaction is not critical. However it is preferred that at least $\frac{1}{2}$ mole of oxygen be used for every mole of iodine. The molar ratio of iodine to benzene which is to be reacted is largely determined by whether one desires to produce a monoiodinated aromatic product or polyiodinated aromatic product. Stoichiometrically, $\frac{1}{2}$ mole of iodine reacts with 1 mole of aromatic compound to produce the monoiodinated form. Similarly on a stoichiometric basis 1 mole of iodine is required to convert 1 mole of aromatic compound to the diiodinated form. Greater or lesser quantities of iodine can be utilized as the artisan may desire. The utilization of excess quantities of iodine result in the product which is contaminated with unreacted iodine. In general, it is desired to run the process to obtain as close to 100% conversion of the iodine as practical so as to simplify the purification steps in the recovery of any unreacted iodine. Suggested mole ratios of aromatic compound to iodine to oxygen are from 1:0.05:0.025 to about 1:2:3. However other ratios may be utilized as desired.

Essentially any source of iodine may be employed including elemental iodine, $I_2$, hydroiodic acid in a gaseous form or alkyl iodines, preferably lower alkyl iodines. Furthermore, mixtures of these materials may be used as the source of iodine.

It is anticipated by the present process would be carried out continuously by the continuous addition of iodine, oxygen and aromatic compound to the reactor, however, the process can be carried out as a batch or semibatch process if desired. Further, the aromatic compound and iodine can be reacted over the catalyst to produce the iodinated product, the addition of the aromatic compound and iodine then being terminated and oxygen then added to the reactor to regenerate the catalyst to its active form and then the process commenced again. Alternatively, in a continuous process it is possible to utilize two reactants circulating the catalyst between them. In the first reactor the iodine and aromatic compound would be added and reacted to form the iodinated compound. The catalyst would then be circulated to the second reactor where it would be contacted with oxygen to be regenerated and then recycled to the first reactor to catalyze additional reactions of aromatic compound with iodine.

The space velocity of the process is not critical and may be readily selected by the artisan. In vapor phase operation, gas hourly space velocities between 10 and 50,000, preferably between 100 and 20,000 liters per hour of reagents per liter of active zeolite, have proven satisfactory.

The catalyst has proven to have an extremely long life and degrades only slowly with time. The degradation of the catalyst is believed to be caused by the combustion of very small quantities of the aromatic compound which deposits small quantities of carbon on the active sites thereby degrading the catalyst activity. When the reaction conditions are selected such that none of the aromatic starting material is oxidized, the life of the catalyst is essentially indefinite.

However, when the catalyst becomes deactivated reactivation is simple. An excellent regeneration technique comprises passing air or oxygen over the catalyst for several hours at elevated temperatures. Typically the temperature is above 400° C. although higher or lower temperatures have proven equally satisfactory. The temperature need only be high enough so as to ensure combustion of the carbon deposit on the catalyst. When pure oxygen is employed lower temperatures can be utilized; when air is employed temperatures on the order of about 400° C. have proven satisfactory. Preferred regeneration temperatures are from about 300°-600° C.

It is advantageous to conduct the catalyst regeneration at lower temperatures since the catalyst degrades if kept at high temperatures for long periods of time. Obviously, the use of lower temperatures is preferred for economic reasons, also.

It has been found that the incorporation of low levels of oxidation catalysts into the non-acid catalyst as noted above substantially decreases the temperature at which catalyst regeneration occurs. Rapid catalyst regeneration is possible, therefore, even though these catalysts do not substantially increase the rate of combustion of the aromatic species during the oxyiodination reaction. While not being limited to any particular theory, it is believed that the presence of iodine during the oxyiodination reaction prevents the oxidation metal from achieving the higher valence states necessary to oxidize aromatic compounds. Under catalyst regeneration conditions, however, only air is fed, and the zeolite is stripped of iodine and the oxidation catalysts thereby become active for the burning off of the carbon deposits.

In addition to non-acid catalysts, it has been found that the inclusion of oxidation catalysts into acidic catalysts improves the regeneration characteristics of the acidic catalysts as well. Acidic catalysts such as, for example, silica-alumina, LZY-72 and SK-500, are within the scope of the present invention. A preferred acidic catalyst is that described in copending application Ser. No. 029,956, filed Mar. 25, 1987 and incorporated herein by reference.

Not all oxidation metals are equally effective in improving the regeneration characteristics of the catalyst. Table 1 presents results in which a deactivated 13X catalyst was treated with the specified amount of oxidation catalyst and was tested at the indicated furnace temperatures. The hot spot temperature is a measure of the activity of the catalyst for the combustion of carbonaceous deposits. Higher hot spot temperatures indicate more efficient regeneration of the catalyst. The most active oxidation catalysts allow regeneration of the catalyst to occur in about 2-4 hours, versus 24-48 hours required for regeneration at the same temperature for an unmodified catalyst.

The lack of effect of the regeneration catalyst on the oxyiodination reaction is demonstrated by measuring the productivity and percent $CO_2$ formed with treated zeolite under standard oxyiodination conditions (100 cc catalyst, 3.0 mmol/min naphthalene, 2.25 mmol/min iodine, 300 ml/min air). For the 13X zeolite containing 0.05% Cr (exchanged on as $CrCl_3$) the percent iodine conversion at 300° C. was identical to that obtained with an untreated catalyst. The percent $CO_2$ was 0.94% versus 0.2-0.5% for the untreated catalyst (each percent $CO_2=0.5\%$ combustion of naphthalene).

TABLE 1

| Oxidation Cat. | Wt. % | Furnace Temp. | Hot Spot Temp. |
|---|---|---|---|
| None | — | 350 | 405 |
| Fe | 0.5 | 350 | 403 |
| Ni | 0.5 | 350 | 404 |
| Pd | 0.1 | 350 | 406 |
| Co | 0.5 | 350 | 410 |
| Mn | 0.5 | 350 | 423 |
| Rh | 0.01 | 350 | 423 |
| V | 0.4 | 350 | 404 |
| Mo | 0.4 | 350 | 422 |
| Ag | 0.4 | 350 | 403 |
| Cu | 0.4 | 350 | 430 |
| Cr | 0.5 | 350 | 493 |
| Cr | 0.05 | 350 | 491 |
| Cr | 0.05 | 325 | 345 |
| Ru | 0.01 | 350 | 496 |
| Ru | 0.01 | 325 | 355 |
| Ru | 0.01 | 300 | 317 |

TABLE 2

| Ex. No. | Temp. °C. | C$_{10}$H$_8$ mmol min$^{-1}$ | I$_2$ mmol min$^{-1}$ | O$_2$ mmol min$^{-1}$ | Catalyst (50 cc) | Products (mole %) C$_{10}$H$_8$ | C$_{10}$H$_7$I | C$_{10}$H$_6$I$_2$ | Wt. % I$_2$ | Vent Gas % CO$_2$ | 2,6/2,7 |
|---|---|---|---|---|---|---|---|---|---|---|---|
| 1 | 225 | 3.0 | 1.5 | 3.0 | K—X | 78.4 | 17.4 | 4.1 | 63.7 | 0.03 | 8.7 |
| 2 | 250 | 3.0 | 1.5 | 3.0 | K—X | 58.9 | 29.0 | 12.2 | 23.3 | 0.04 | 4.5 |
| 3 | 300 | 3.0 | 1.5 | 3.0 | K—X | 10.1 | 45.3 | 36.1 | 1.2 | 0.2 | 2.2 |
| 4 | 200 | 3.0 | 1.5 | 3.0 | 1% V$_2$O$_5$—KX | 52.9 | 32.1 | 13.0 | 35.5 | 0.03 | — |
| 5 | 220 | 3.0 | 1.5 | 3.0 | 1% V$_2$O$_5$—KX | 34.6 | 46.0 | 17.0 | 23.8 | 0.036 | — |
| 6 | 250 | 3.0 | 1.5 | 3.0 | 1% V$_2$O$_5$—KX | 27.7 | 52.9 | 19.3 | 8.4 | 0.11 | 4.0 |
| 7 | 300 | 3.0 | 1.5 | 3.0 | 1% V$_2$O$_5$—KX | 9.7 | 43.6 | 37.1 | 0.8 | 0.45 | — |
| 8 | 250 | 3.0 | 1.5 | 3.0 | NaX | 77.3 | 14.7 | 7.9 | 59.0 | 9.7 | — |
| 9 | 250 | 3.0 | 2.25 | 4.5 | 1% FeSO$_4$—KX | 3.1 | 42.9 | 42.0 | 8.1 | 0.16 | — |
| 10 | 250 | 3.0 | 2.25 | 4.5 | 1% CrCl$_3$—KX | 4.4 | 59.8 | 34.8 | 6.4 | 0.12 | — |
| 11 | 220 | 3.0 | 2.25 | 4.5 | 0.2% CuCl$_2$—KX | 4.0 | 28.1 | 53.3 | 6.1 | 0.15 | 4.7 |
| 12 | 250 | 3.0 | 2.25 | 4.5 | 0.5% MoO$_3$—KX | 6.0 | 35.4 | 43.2 | 11.3 | 0.09 | — |
| 13 | 225 | 3.0 | 1.5 | 3.0 | 10% KF—Al$_2$O$_3$ | 83.0 | 10.9 | 6.1 | 50.7 | 0.03 | |
| 14 | 225 | 3.0 | 1.5 | 3.0 | 10% KF—1% FeSO$_4$—Al$_2$O$_3$ | 65.4 | 25.3 | 9.3 | 42.4 | 0.03 | |

TABLE 3

| Ex. No. | Temp. °C. | C$_6$H$_6$ mmol min$^{-1}$ | I$_2$ mmol min$^{-1}$ | O$_2$ mmol min$^{-1}$ | Catalyst (50 cc) | Products (mole %) C$_6$H$_6$ | C$_6$H$_5$I | C$_6$H$_4$I$_2$ | Wt. % I$_2$ | Vent Gas % CO$_2$ |
|---|---|---|---|---|---|---|---|---|---|---|
| 15 | 300 | 5.6 | 1.5 | 5.0 | K—X | 77.7 | 17.8 | 4.5 | 23.0 | 0.30 |
| 16 | 300 | 5.6 | 1.5 | 5.0 | 0.2% CoCl$_2$—KX | 66.7 | 21.4 | 11.6 | 7.8 | 0.35 |
| 17 | 300 | 5.6 | 1.5 | 5.0 | 0.3% H$_3$BO$_3$—KX | 65.2 | 21.5 | 13.3 | 4.7 | 0.38 |

Oxidation catalyst which are preferred for improving the regeneration characteristics of a catalyst are Co, Mn, Rh, Mo, Cu, Cr and Ru. Particularly preferred are ruthenium (Ru) and chromium (Cr).

By combining oxidation catalysts which give good activity and selectivity in the oxyiodination reaction with catalysts which are preferred for improving the regeneration characteristics of a catalyst, an oxyiodination catalyst can be designed and fine-tuned for any particular reactants and reaction conditions. In other words, by combining one or more oxidation catalysts such as sodium, potassium, rubidium, and cesium which are preferred oxidation catalysts for the oxyiodination of naphthalene, with one or more oxidation catalysts such as ruthenium and chromium, which are preferred catalysts for improving regeneration, a composite catalyst can be designed which is active in the oxyiodination reaction, gives minimal combustion, and also has improved regeneration characteristics. The particular oxidation catalysts and the particular mixtures of these catalysts will depend on the specific reactant and reaction conditions which are employed. These conditions can be easily determined by routine experimentation.

The incorporation of an oxidation catalyst into the base catalyst, therefore, has multiple benefits. The activity and selectivity of the catalyst during the oxyiodination reaction are improved and the amount of time and energy required to regenerate the catalyst is also improved. By using mixtures of oxidation catalysts, the properties of the oxyiodination catalyst can be tailored to a wide variety of aromatic compounds and reaction conditions.

The examples in Tables 2 and 3 are presented to illustrate the present invention but are not intended in any way limit the scope of the invention which is defined by the appended claims.

While the invention has been described in detail with particular reference to preferred embodiments thereof, it will be understood that variations and modifications can be effected within the spirit and scope of the invention.

What is claimed as new and desired to be secured by Letters Patent of the United States is:

1. A process for oxyiodinating a hydrocarbon aromatic compound, comprising:

reacting a hydrocarbon aromatic compound with iodine in the presence of oxygen over a combined catalyst, said combined catalyst comprising an iodination catalyst selected from the group consisting of zeolites, acidic silica-aluminas and alumina, silica, silica-alumina and titania inert supports containing alkali or alkaline earth cations, and containing less than about 1 wt. % of an oxidation catalyst selected from the group consisting of Rh, Cr, Ru cations and mixtures thereof, to produce an iodoaromatic compound, wherein said reacting is continued until said combined catalyst is at least partially deactivated by carbon deposits;

separating said hydrocarbon aromatic compound and iodine from said deactivated combined catalyst; and heating said deactivated catalyst in the presence of an amount of oxygen, at a temperature and for a time sufficient to remove the carbon deposits by combustion to produce a regenerated combined catalyst.

2. The process of claim 1, wherein said oxidation catalyst is Cr.

3. The process of claim 1, wherein said oxidation catalyst is Ru.

4. The process of claim 1, wherein said heating step is conducted at a temperature between 300°–500° C.

5. The process of claim 1, wherein said oxygen is in the form of pure oxygen, air, or oxygen diluted with an inert gas or vapor.

6. The process of claim 1, wherein said heating is performed for about 2–10 hours.

7. The process of claim 6, wherein said heating is conducted for about 2–4 hours.

8. The process of claim 1, wherein said combined catalyst comprises less than 0.5 wt. % of said oxidation catalyst.

9. The process of claim 1, wherein said iodination catalyst is a zeolite.

10. The process of claim 9, wherein said zeolite is a non-acid zeolite.

11. The process of claim 10, wherein said non-acid zeolite is an X or Y-zeolite.

12. The process of claim 1, wherein said iodination catalyst is acidic silica-alumina.

13. The process of claim 1, wherein said iodination catalyst comprises alkali or alkaline earth cations on an inert support.

14. The process of claim 1, wherein said hydrocarbon aromatic compound is selected from the group consisting of benzene, biphenyl, naphthalene, and anthracene.

15. The process of claim 1, wherein said aromatic compound is benzene.

16. The process of claim 1, wherein said aromatic compound is naphthalene.

* * * * *